US00PP14261P39

(12) United States Plant Patent
Jones

(10) Patent No.: US PP14,261 P3
(45) Date of Patent: Nov. 4, 2003

(54) NEMESIA PLANT NAMED 'PENGOON'

(50) Latin Name: *Nemesia*
Varietal Denomination: Pengoon

(76) Inventor: Sidney James Jones, PenHow Nursery Carron Hill, St. Bridges Netherwent Magor Caldicot South Wales (GB), NP26 3AU ( * ) Notice: Subject to any disclaimer, the term of this patent is extended or adjusted under 35 U.S.C. 154(b) by 0 days.

(21) Appl. No.: 10/036,197

(22) Filed: Dec. 28, 2001

(65) Prior Publication Data

US 2003/0126657 P1 Jul. 3, 2003

(51) Int. Cl.[7] ..... A01H 5/00

(52) U.S. Cl. ..... Plt./263

(58) Field of Search ..... Plt./263

*Primary Examiner*—Kent Bell

(57) ABSTRACT

A new and distinct cultivar of Nemesia plant named 'Pengoon' that is characterized by a compact dense habit, dense upright spikes of sweet scented blue-purple flowers each with a red-purple palate, and oval shaped green leaves. In combination these characteristics set 'Pengoon' apart from all other existing varieties of Nemesia known to the inventor.

2 Drawing Sheets

Genus/species: Nemesia hybrid.
Denomination: 'Pengoon'.

BACKGROUND OF THE INVENTION

The present invention relates to a new and distinct cultivar of Nemesia plant known botanically as Nemesia hybrid and that will be referred to hereinafter by the cultivar name 'Pengoon'.

The new Nemesia is a product of a planned breeding program conducted by the Inventor in Netherwent, Wales. The breeding program objectives were to improve upon well-known varieties such as *Nemesia denticulata* 'Confetti' (unpatented), *Nemesia caerulea* 'Innocence' (unpatented), *Nemesia caerulea* 'Joan Wilder' (unpatented), *Nemesia caerulea* 'Woodcote' (unpatented), and *Nemesia caerulea* 'Elliott's' (unpatented). The goals of the breeding program were to improve on plant habit by breeding plants that were more compact, with stiff, upright flower spikes, increase the size of the flower and the length of flowering time, improve the color range by producing clear colors, and produce plants that root readily and consistently from vegetative stem cuttings.

The new Nemesia originated from a cross-pollination made by the Inventor in 1996 of an unnamed and unpatented Nemesia hybrid, as the female, or seed, parent with an unnamed and unpatented Nemesia hybrid, as the male, or pollen, parent. The cultivar 'Pengoon' was discovered and selected by the Inventor as a plant within the progeny from this cross-pollination in a controlled environment in Netherwent, Wales, in 1996.

'Pengoon' is distinguishable from the parent plants by its compact, dense habit, blue-purple flowers, and dense upright flower spikes. 'Pengoon' differs from all other Nemesia known to the inventor, by its leaves that are more oval in shape and exhibit thicker tissue. Mature stems grow in square shape rather than round shape and the flowers have a faint perfume scent. The flowers exhibited by 'Pengoon' contain purple in the blue color, which is not seen in any other upright Nemesia known to the inventor. When looking at the flowers of 'Pengoon' mor blue-purple is apparent in the overall appearance of the flower because the palate in the center of the flower is red-purple whereas other varieties of blue flowered Nemesia known to the inventor have a yellow palate in the center of the flower.

'Pengoon' was first asexually propagated by the Inventor in 1997 in a cultivated area or Netherwent, Wales using vegetative stem cuttings and has shown that the unique features of this new Nemesia plant are stable and reproduced true to type in successive generations of asexual reproduction.

SUMMARY OF THE INVENTION

The following traits have been repeatedly observed and represent the distinguishing characteristics of 'Pengoon'. In combinaton these traits set the new cultivar apart from all other existing varieties of Nemesia known to the inventor. 'Pengoon' has not been tested under all possible conditions and phenotypic differences may be observed with variations in environmental, climatic, and cultural conditions, however, without any variance in genotype.

1. Nemesia 'Pengoon' exhibits a compact dense habit.
2. Nemesia 'Pengoon' exhibits blue-purple flowers with a red-purple palate in the center of each individual flower.
3. Nemesia 'Pengoon' exhibits upright fragrant flower spikes.
4. Nemesia 'Pengoon' is floriferous and exhibits large, repeat-flowering heads.
5. Nemesia 'Pengoon' is hardy to minus 5° Centigrade.

BRIEF DESCRIPTION OF THE DRAWINGS

The accompanying color drawings illustrate the overall appearance of the new Nemesia cultivar 'Pengoon' showing the colors as true as it is reasonably possible to obtain in colored reproductions of this type. Colors in the drawings may differ from the color values cited in the detailed botanical description which accurately describe the actual colors of the new variety 'Pengoon'. Plants are 12-months-old, in two-liters containers and were grown under greenhouse conditions in Encinitas, Calif.

The drawing on sheet 1 illustrates the entire plant and habit from a side perspective.

The drawing on sheet 2 is a close-up view of the flowers. The drawings were made using conventional photographic techniques and the laser prints were made using standard laser printing techniques. Although colors may appear different from actual colors due to light reflectance, they are as accurate as possible by conventional photography and laser printing.

BOTANICAL DESCRIPTION OF THE PLANT

The following is a detailed description of the Nemesia plant named 'Pengoon'. Data was collected in Arroyo Grande, Calif. from 12-month-old plants grown indoors in two-liters containers under greenhouse conditions. Phenotypic differences may be observed with variations in environmental, climatic, and cultural conditions. The color determinations are in accordance with The Royal Horticultural Society Colour Chart except where general color terms of ordinary dictionary significance are used. The growing requirements are similar to other Nemesia plants.

Botanical classification: Nemesia 'Pengoon'.
Species: Hybrid.
Common name: Nemesia.
Use: Bedding and patio plant.
Parentage: The parents of Nemesia 'Pengoon' are unnamed Nemesia hybrids.
- *Female parent.*—Unnamed Nemesia hybrid.
- *Male parent.*—Unnamed Nemesia hybrid.

Propagation: Vegetative stem cuttings.
Sexuality: Hermaphrodite.
Growth habit: Compact dense habit.
Plant dimensions: 36 cm. in height and 64 cm. in width.
Type: Hardy perennial.
Time to initiate roots: Approximately 16 days at temperatures of 21° Centigrade is required to produce rooted cuttings.
Crop time: 12 months are required to produce a finished two-liters product from a rooted cutting.
Root system: Numerous and fine.
Hardiness: Hardy to minus 5° Centigrade.
Disease and pest susceptibility and resistance: There are no disease problems known to the inventor other than what affects typical Nemesia.
Stem:
- *Stem shape.*—Quadrilateral with ridges.
- *Stem length.*—39 cm. in length.
- *Stem diameter.*—3 mm. in diameter.
- *Stem surface.*—Glabrous.
- *Stem color.*—144A.
- *Internode length.*—2–5 cm. between nodes.
- *Branching.*—Ascending and freely branching.

Foliage:
- *Leaf shape.*—Oval.
- *Leaf division.*—Simple.
- *Apex.*—Acute.
- *Base.*—Rounded.
- *Margin.*—Crenulate.
- *Surface.*—Glabrous.
- *Arrangement.*—Opposite.
- *Leaf length.*—2.5 cm. in length.
- *Leaf width.*—1.25 cm. in width.
- *Leaf color* (*adaxial surface*).—137B.
- *Leaf color* (*abaxial surface*).—147B.
- *Leaf attachment.*—Most of the leaves are sessile, although some of the leaves exhibit a very small petiole.
- *Petiole color* (*adaxial surface*).—137B.
- *Petiole color* (*abaxial surface*).—147B.
- *Petiole dimensjons.*—2 mm. in length and 3 mm. in width.
- *Vein pattern.*—Parallel.

Flowers:
- *Flowering season.*—Spring and summer.
- *Fragrance.*—Faint perfume fragrance.
- *Self-cleaning or persistent.*—Self-cleaning.
- *Inflorescence dimensions.*—7 cm in length and 3 cm. in width.
- *Type of inflorescence.*—Axillary raceme.
- *Number of flowers per inflorescence.*—30 flowers per inflorescence.
- *Pedicel dimensions.*—9 mm. in length and 0.50 mm. in diameter.
- *Pedicel surface.*—Stipitate glandular.
- *Pedicel color.*—144A.
- *Peduncle dimensions.*—10 cm. in length and 3 mm. in width.
- *Peduncle surface.*—Glabrous.
- *Peduncle color.*—138A.
- *Bud shape.*—Flattened oval.
- *Bud color.*—80A.
- *Bud dimensions.*—6 mm. in length and 4 mm. in diameter.
- *Flower color* (*adaxial surface*).—90C.
- *Flower color* (*abaxial surface*).—91C.
- *Flower shape.*—Personate.
- *Plate color.*—N87D.
- *Throat color.*—91C.
- *Nectary* (*located on inside of palate*).—4 mm. in width and 4 mm. in length.
- *Color of nectary.*—1C.
- *Flower dimensions.*—16 mm. in length, 2 cm. in width at the widest part and 0.75 cm. in depth.
- *Lower lip dimensions.*—1 cm. in width and 9 mm. in length.
- *Lobe dimensions* (*each lobe of lower lip*).—9 mm. in length and 0.50 cm. in width.
- *Upper lip dimensions.*—2 cm. in width and 7 mm. in length.
- *Lobe dimensions* (*each lobe of upper lip*).—7 mm. in length and 5 mm. in width.
- *Lip surface.*—Glabrous.
- *Lip margin.*—Entire.
- *Lip apex* (*upper and lower lips*).—Lobed with each lobe having a rounded apex.
- *Lip base* (*upper lip and lower lips*).—Truncate.
- *Lips.*—Two lips in number. The upper lip has four lobes and the lower lip is bilabiate.
- *Lips fused or unfused.*—Basally fused.
- *Color of upper lip* (*adaxial surface*).—90C.
- *Color of upper lip* (*abaxial surface*).—91C.
- *Color of lower lip* (*adaxial surface*).—90C.
- *Color of lower lip* (*abaxial surface*).—91C.
- *Flower spur dimensions.*—6 mm. in length and 2 mm. in diameter.
- *Spur color.*—85D.

*Calyx dimensions.*—3 mm. in length and 6 mm. in width.
*Sepal dimensions.*—3 mm. in length and 1.50 mm. in width.
*Sepals.*—Five in number.
*Sepal surface* (*adaxial surface*).—Stipitate glandular.
*Sepal surface* (*abaxial surface*).—Stipitate glandular.
*Sepal apex.*—Acute.
*Sepal margin.*—Entire.
*Sepal color* (*adaxial surface*).—144A.
*Sepal color* (*abaxial surface*).—144A.
*Lastingness of individual flower.*—An average of 2 weeks.

Reproductive organs:
*Stamens.*—Two in number with filaments curved around one another.
*Color of stamens.*—155A.
*Stamen dimensions.*—3 mm. in length and less than 1 mm. in diameter.
*Anther color.*—161A.
*Anther dimensions.*—Less than 0.50 mm. in length and less than 0.50 mm. in width.
*Amount of pollen.*—Moderate.
*Color of pollen.*—6B.
*Pistil.*—One.
*Pistil color.*—155A.
*Pistil dimensions.*—0.25 mm. in length and 0.25 mm. in diameter.
*Ovary dimensions.*—0.50 mm. in length and 0.50 mm. in width.
*Ovary shape.*—Oval to round.
*Ovary position.*—Superior.
*Ovary color.*—145A.

Seed production:
*Quantity of seed.*—Approximately 15 fertile seeds per capsule.
*Capsules.*—Approximately 20 capsules per flowering spike, but this is markedly influenced by how many times the plant is pinched back.
*Capsule dimensions.*—12 mm. in length and 7 mm. in width.
*Capsule color.*—177D.
*Capsule surface.*—Glossy.
*Appearance of seed.*—Flattened and winged.
*Seed color.*—200D and wing 156D.
*Shape of seed.*—Oval.
*Seed dimensions.*—3 mm. in length and 2.5 mm. in width.

I claim:

1. A new and distinct cultivar of Nemesia plant named 'Pengoon' as described and illustrated herein.

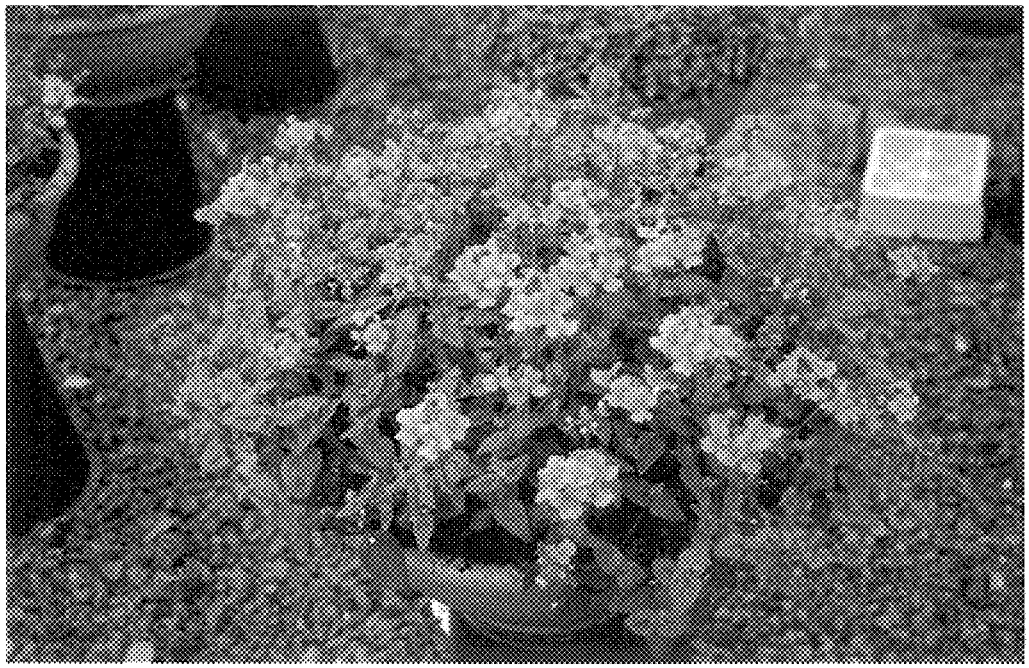

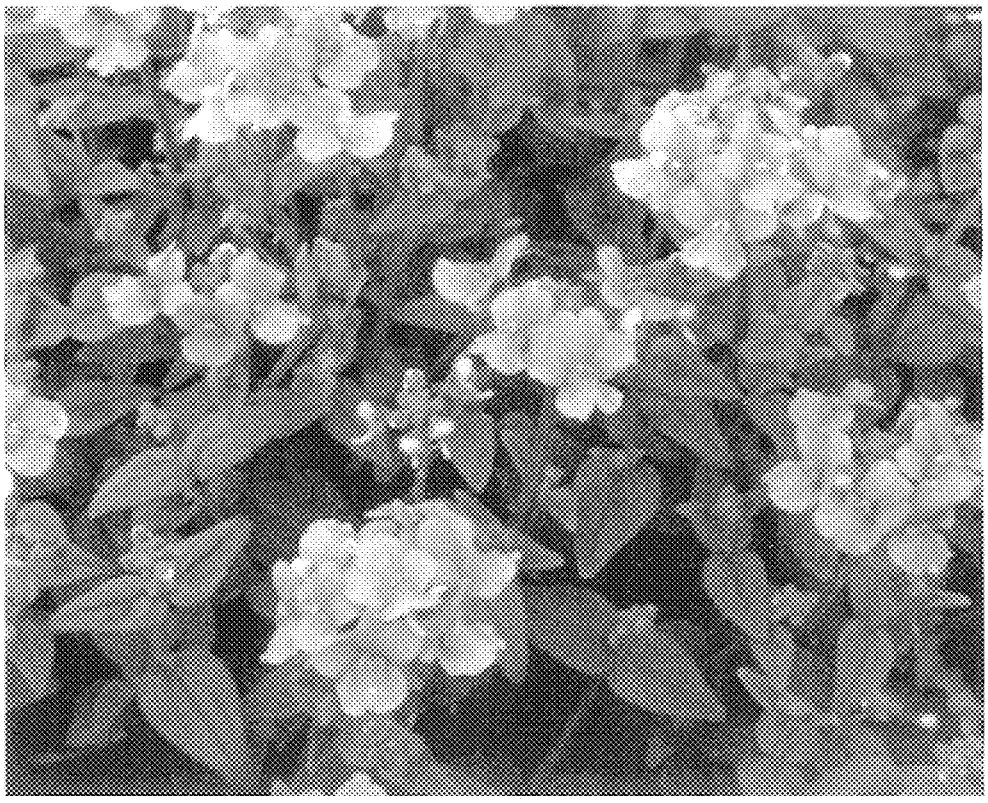

* * * * *